United States Patent [19]

Murtha et al.

[11] 4,383,940

[45] May 17, 1983

[54] CATALYSTS FOR HYDROGENATION OF UNSATURATED DINITRILES

[75] Inventors: Timothy P. Murtha, Bartlesville; Charles A. Drake, Nowata, both of Okla.

[73] Assignee: Phillips Petroleum Company, Bartlesville, Okla.

[21] Appl. No.: 326,108

[22] Filed: Nov. 30, 1981

Related U.S. Application Data

[62] Division of Ser. No. 213,444, Dec. 5, 1980, Pat. No. 4,311,859.

[51] Int. Cl.$^3$ .................... B01J 21/08; B01J 23/46
[52] U.S. Cl. .................................................. 252/460
[58] Field of Search ................ 252/460, 466 PT, 472

[56] References Cited

U.S. PATENT DOCUMENTS 4,162,262  7/1979  Ellgen et al. .................. 252/460 X
4,186,110  1/1980  Jalan et al. .................... 252/460 X

FOREIGN PATENT DOCUMENTS 11476  5/1980  European Pat. Off. ............ 252/460

Primary Examiner—Carl F. Dees

[57] ABSTRACT

Unsaturated dinitriles are hydrogenated to saturated diamines using a rhodium catalyst on a silica support having a surface area larger than 275 $m^2/g$, a pore volume of from about 1.0 to 1.5 mL/g and an average pore size of from about 100 to about 175 Å. The supported rhodium catalyst is prepared by a method which includes the steps of contacting a silica support having the characteristics described above with a solution or dispersion of rhodium or a reducible compound of rhodium, and then subjecting the impregnated silica support to vacuum treatment.

9 Claims, No Drawings

CATALYSTS FOR HYDROGENATION OF UNSATURATED DINITRILES

This is a divisional of pending application Ser. No. 213,444, filed Dec. 5, 1980, now U.S. Pat. No. 4,311,859.

BACKGROUND

This invention relates to the preparation of saturated aliphatic diamines by the catalytic hydrogenation of unsaturated aliphatic dinitriles. It further relates to a catalyst composition effective in the hydrogenation of unsaturated aliphatic dinitriles to saturated aliphatic diamines.

In general, various processes for the catalytic hydrogenation of unsaturated aliphatic dinitriles to saturated aliphatic diamines are known in the art. Supported Group VIII metal catalysts such as cobalt, nickel, ruthenium, rhodium or palladium have been employed as catalysts for hydrogenating various feedstocks in these processes. The hydrogenation of branched-chain unsaturated aliphatic dinitriles in the presence of supported rhodium catalysts is disclosed in U.S. Pat. No. 3,880,928. It has been found that these Group VIII metal hydrogenation catalysts differ in their effectiveness and efficiency in hydrogenating unsaturated aliphatic dinitriles of the formula

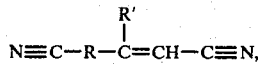

wherein each R is an alkylene or an alkylidene radical and R' is an alkyl radical. For example, some supported metal hydrogenation catalysts have insufficient physical stability or low catalytic activity under conditions present during the dehydrogenation reaction.

It is an object of this invention to provide a method for the hydrogenation of unsaturated aliphatic dinitriles. It is a further object to provide a supported metal catalyst for the hydrogenation of unsaturated aliphatic dinitriles which is both stable under hydrogenation reaction conditions and has high catalytic activity. It is a further object to provide a method of preparing a stable supported rhodium hydrogenation catalyst.

SUMMARY OF THE INVENTION

According to the invention, unsaturated aliphatic dinitriles are reacted with hydrogen in the presence of a catalyst comprising rhodium on a silica support, the support being characterized by a surface area of at least about 275 m²/g, a pore volume of about 1.0 to about 1.5 mL/g, and an average pore size of about 100 to about 175 Å. Also according to the invention, a hydrogenation catalyst is prepared by impregnating a silica support having the characteristics described above with a solution or dispersion of rhodium or a reducible compound of rhodium, and then subjecting the impregnated silica support to vacuum treatment. The resulting supported catalyst shows high activity, relatively slow activity decline, and good stability under hydrogenation conditions.

DETAILED DESCRIPTION OF THE INVENTION

The branched-chain unsaturated aliphatic dinitriles which are hydrogenated in accordance with the process of the invention are the unsaturated dinitriles of the formula

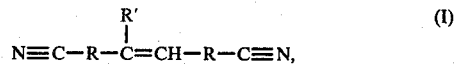

wherein each R is independently selected from alkylene radicals and alkylidene radicals and R' is an alkyl radical. Each R will generally have from 1 to 15 carbon atoms, preferably 1 to 6, and commonly 1 to 3 carbon atoms. R' will generally have from 1 to 15 carbon atoms, preferably from 1 to 6, and commonly from 1 to 3 carbon atoms. In general, the unsaturated dinitrile reactant of Formula I will contain from 7 to 30 carbon atoms, preferably from 8 to 16, and commonly from 9 to 12 carbon atoms.

Representative unsaturated dinitriles of Formula I include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-3-dodecenedinitrile, 2,4,7,9,11,13,15-heptaethyl-6-hexadecenedinitrile, and mixtures of these.

If desired, other unsaturated dinitrile reactants can be present and effectively hydrogenated during the hydrogenation of the unsaturated dinitriles of Formula I. Thus, the dinitrile feedstock can contain one or more unsaturated dinitrile reactants of the formula

wherein each R" is independently selected from alkylene radicals and alkylidene radicals. In general, each R" will have from 1 to 15 carbon atoms, preferably from 1 to 7, and commonly from 1 to 4 carbon atoms. The dinitriles of Formula II will generally contain from 6 to 30 carbon atoms, preferably from 8 to 16, and commonly from 9 to 12 carbon atoms. Representative unsaturated dinitrile compounds of Formula II include 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,6-dimethyl-4-methyleneheptacosanedinitrile, and mixtures of these.

Unsaturated dinitriles having structures other than those of Formulas I and II may be present during the hydrogenation reaction. Also, other compounds which may be found in the feed source of the dinitriles of Formulas I and II can be present so long as these additional compounds do not have a significant adverse effect on the hydrogenation of the dinitriles of Formulas I and II. Where other dinitriles are present in the feedstock, the dinitriles of Formula I will generally constitute at least 0.1 weight percent of the total dinitriles. The significant advantages of the invention increase with increasing concentration of the dinitriles of Formula I in the feedstock. The presence of dinitriles of Formula I in an amount of at least 10 weight percent of the feedstock is particularly desirable.

The presently preferred branched-chain unsaturated aliphatic dinitrile feedstock for use in the invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of Formula I, while the last three compounds are of the type of Formula II. The weight ratio of the dinitriles of Formula I to the dinitriles of Formula II in this mixture is generally in the range of about 10:1 to 1:10.

In the practice of the invention, the catalytic hydrogenation of the unsaturated dinitrile reactant of Formula I results primarily in the production of saturated diamine reaction products having the formula

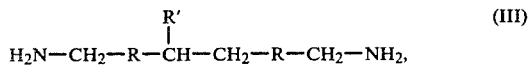

$$H_2N-CH_2-R-CH(R')-CH_2-R-CH_2-NH_2, \quad (III)$$

wherein R and R' are as defined previously. The catalytic hydrogenation of the unsaturated dinitrile reactant of Formula II results primarily in the formation of saturated diamine reaction products having the formula

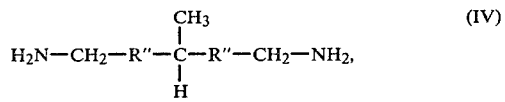

$$H_2N-CH_2-R''-C(CH_3)(H)-R''-CH_2-NH_2, \quad (IV)$$

wherein R" is as defined previously.

The catalysts of the invention comprise silica-supported rhodium. The rhodium component includes finely-divided elemental rhodium and compounds of rhodium which are reducible by hydrogen to finely-divided elemental rhodium, and mixtures of these. Suitable reducible compounds include, for example, the oxides, halides, nitrates, oxalates, acetates, carbamates, propionates, tartrates, hydroxides, and mixtures of these. Specific examples include rhodium carbonate, rhodium oxide, rhodium chloride, rhodium nitrate, rhodium oxalate, rhodium acetate and rhodium hydroxide.

The weight ratio of catalyst to unsaturated dinitrile reactant, based on the weight of the total of rhodium contained, can be varied as desired. For the purpose of maintaining reasonable reaction rates under economical catalyst reaction kinetics in a batch reaction, it is generally preferred that the weight ratio of rhodium to the unsaturated dinitrile reactants be maintained within a range of about 0.01:100 to about 30:100, preferably in the range of about 0.1:100 to about 20:100.

The rhodium catalyst of the invention is supported on a silica support. The silica support contains greater than about 80 weight percent silica and preferably more than 95 weight percent silica. The silica support can be in the form of spheres, extrudates, pellets, granules, and the like. The size of the catalyst support will depend upon the equipment used and the feed rate and can be any size that results in an acceptable hydrogenation reaction. In general, the size of the support will be in the range of about 0.5" in diameter to about 50 mesh (U.S. Standard Sieve Series, ASTM Specification E-11-61). In a continuous process the limit on the finer size will be determined by excessive pressure drop in the hydrogenation column and the limit on the coarser size will be determined by excessive channeling of the feed between catalyst particles.

The silica supports have been found to require certain characteristics in order to provide the desired high catalytic activity and stability observed with the invention. The surface area of the silica supports of the invention will be generally larger than about 275 m$^2$/g, determined by the BET method using gas adsorption, preferably nitrogen adsorption. The silica support has a pore volume within a range of about 1.0 to about 1.5 mL/g, preferably from about 1.0 to about 1.3 mL/g, as determined by water adsorption using the Innes method. The average pore size of the silica support will be generally from about 100 to about 175 Å and preferably will be from about 110 to about 150 Å, as calculated from the pore size distribution as determined by mercury porosimetry.

The catalyst support can be prepared by any suitable means. For example, larger bodies of the support material can be crushed and screened to the desired size. Alternately, the support can be prepared in the form of pellets, extrudates and the like using conventional techniques. An example of a commercially available silica support exhibiting the desired characteristics and producing a catalyst having high activity and good stability is a G59 support from Davison Chemical Division of W. R. Grace & Co.

In batch hydrogenations, the elemental rhodium content of the supported catalyst will generally be in the range of about 0.1 to about 30 weight percent, preferably in the range of about 0.5 to about 10 weight percent, based on the weight of the catalyst support. In continuous hydrogenations, the elemental rhodium content will generally be in the range of about 0.01 to about 10 weight percent, preferably in the range of about 0.05 to about 5 weight percent, based on the weight of the catalyst support.

The supported rhodium catalyst of the invention is prepared by a procedure involving impregnation of the support material with rhodium or a rhodium compound and subsequent vacuum treatment. The support is first impregnated with a solution or dispersion of rhodium in elemental form or in the form of compounds reducible to rhodium. As used herein, the term "solution" includes dispersions and other systems in which a soluble or insoluble rhodium compound is distributed in a liquid medium. The presently preferred method of impregnation involves the use of a solution of reducible compounds of rhodium. Generally the solution is contacted with the support for a time of about 2 to about 24 hours and the solvent is removed under reduced pressure to yield an impregnated support.

The impregnated support is then treated under vacuum. The vacuum used will generally be in the range of about 10$^{-4}$ to about 50 mm Hg and will preferably be within the range of about 10$^{-2}$ to 20 mm Hg. During the vacuum treatment step, the temperature will generally be within the range of about 20° to about 250° C. and preferably will be within the range of about 40° C. to about 200° C. The vacuum treatment will generally be carried out for a period of about 15 minutes to about 30 hours, preferably for a time within the range of about 1 hour to about 24 hours.

Following the vacuum treatment, the impregnated support can be reduced with hydrogen or other suitable reducing agents such as hydrazine or sodium borohydride, or the reduction can be achieved in the hydrogenation reactor. Generally, if hydrogen is used, the reduction is carried out at atmospheric pressure at a temperature in the range of about 100°–500° C. for a time which can vary from about 15 minutes to about 10 hours.

The invention catalyst has been found to exhibit high activity in the one-step hydrogenation of unsaturated dinitriles at both the olefinic and nitrile sites. By "high activity" in this context is meant that the hydrogenation reaction product contains no more than about 5 weight percent unsaturated diamine reaction product, based on the total weight of unsaturated and saturated diamines, using fresh catalyst and after an initial reaction time of four hours. Unsaturated dinitrile hydrogenation catalyst are known to undergo a fairly rapid decline in activity with use. The invention catalyst also is subject to a reduction in activity with use, but the decline is less rapid than is observed for rhodium on other silica supports. An improvement in the active life of rhodium catalysts is particularly important because little success has been realized in attempting to regenerate such catalysts by conventional catalyst regeneration procedures. A further problem with supported hydrogenation catalysts is the tendency of some catalysts to deteriorate under the conditions of temperature and pressure in the hydrogenation reactor. The invention catalyst has been found to be durable over the test reaction period, in contrast with certain other rhodium catalysts, particularly alumina-supported rhodium, which showed a tendency to collapse to powder during test runs. The invention catalyst thus exhibits a combination of the properties of high activity, slow activity decline, and durability.

Any catalytic hydrogenation temperature can be employed which provides the desired degree of catalytic efficiency in the hydrogenation of the branched-chain unsaturated aliphatic dinitrile. The hydrogenation temperature will generally be within the range of about 30° C. to about 180° C. The most effective catalytic hydrogenation temperatures are considered to be within the range of about 70° C. to about 150° C.

The catalytic hydrogenation of branched-chain unsaturated aliphatic dinitriles can be carried out at any hydrogen pressure at which both the olefinic unsaturation and the nitrile group are reduced in the presence of ammonia, hydrogen and a suitable diluent. Generally, suitable hydrogen pressures are within the range of about 200 to about 5000 psig, but lower or higher hydrogen pressures can be used. Preferably, due to economic considerations, hydrogen pressures within the range of about 500 to about 3000 psig are used.

Any time period suitable for the catalytic hydrogenation of branched-chain unsaturated aliphatic dinitriles can be used in the practice of the invention. However, the most economical time periods for a batch hydrogenation process are generally within the range of about 15 minutes to about 5 hours. A reaction time in the range of about 1 to 3 hours is presently preferred in order to insure hydrogenation of unsaturated olefinic bonds in the feedstock as well as complete hydrogenation of the nitrile groups to primary amino groups. The catalytic hydrogenation of unsaturated dinitriles in accordance with the process of the invention can be carried out as a continuous process at any suitable liquid hourly space velocity. However, the liquid hourly space velocity rates will generally be within the range of about 0.1 to about 20, preferably from about 0.5 to about 20, volumes of unsaturated dinitrile reactant plus diluent and ammonia per volume of catalyst (including the volume of the catalyst support).

The diluent is selected from saturated aliphatic alcohols containing 1 to 12 carbon atoms per molecule, alkanes and cycloalkanes having from 4 to 12 carbon atoms, and unsubstituted cyclic ethers having from 4 to 12 carbon atoms, and mixtures of these. The term "unsubstituted" means that there are no substituents other than hydrocarbyl radicals. Examples of alcohol diluents include methanol, ethanol, 2-propanol, 2-methyl-2-propanol, 2-methyl-2-butanol, 2-ethyl-2-hexanol, 2-butanol, 1-hexanol, 1-octanol, 2-decanol, and 1-dodecanol. Examples of alkanes and cycloalkanes include butane, pentane, hexane, decane, dodecane, cyclobutane, cyclopentane, cyclohexane, cyclodecane, cyclododecane, 2-methylbutane, methylcyclopentane, 2,2,4-trimethylpentane and mixtures of these. Examples of ethers include 1,3-dioxane, 1,4-dioxane, tetrahydrofuran, 4,4-dimethyl-1,3-dioxane, and mixtures of these. Presently preferred diluents are aliphatic tertiary alcohols containing 4 to 12 carbon atoms per molecule. Examples of such aliphatic tertiary alcohols include 2-methyl-2-propanol, 2-methyl-2-butanol, 3-ethyl-3-hexanol, 2,4-dimethyl-2-pentanol, 2,3-dimethyl-3-pentanol, and 3,7-dimethyl-3-octanol. The currently preferred solvent is 2-methyl-2-propanol. To facilitate handling of the reaction mixtures, the weight ratio of unsaturated dinitrile reactants to diluent charged to the reaction zone is generally within the weight ratio range of about 0.001:100 to about 25:100 and is preferably in the range of about 0.1:100 to about 20:100.

Ammonia is used in the process of the invention as a means of suppressing undesirable side reactions such as the formation of secondary and tertiary amines. Any amount of ammonia can be used which is effective in eliminating or reducing undesirable side reactions. In general, the mole ratio of ammonia to cyano group (there being two cyano groups in each unsaturated dinitrile) will be in the range of about 1:1 to about 25:1, preferably in the range of about 7:1 to about 15:1.

Recovery of the desired end product, the branched-chain saturated aliphatic diamines as well as any resulting reaction by-products, any unconsumed reactants, ammonia, hydrogen, and diluents can be effected by any conventional separation means. In general, at the conclusion of the catalytic hydrogenation in a batch process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the saturated diamines can be conveniently separated from any reaction by-products or any diluent remaining in the filtrate by any conventional fractional distillation.

In a continuous hydrogenation process, the reactor effluent is depressured and separated by conventional separation methods such as fractional distillation to separate the ammonia, diluent, reaction products, and any reaction by-products. The ammonia and diluent can be recycled to the hydrogenation zone if desired.

The branched-chain saturated aliphatic diamine products of the process of the invention are useful for the preparation of polymers such as polyamide polymers. The terephthalamide polymers prepared from terephthalic acid and the branched-chain saturated diamine products of the invention have been found to be useful in making fibers and engineering plastics.

EXAMPLES

In the following examples, the hydrogenation substrate which is undergoing hydrogenation is an olefinically unsaturated dinitrile mixture prepared from isobutylene and acrylonitrile. The mixture contained approximately 52 weight percent 5-methylenenonanedinitrile, approximately 35 weight percent 5-methyl-4-nonenedinitrile, approximately 12 weight percent of the combination of 2,4-dimethyl-4-octenedinitrile, 2-methyl-4-methyleneoctanedinitrile, and 2,4-dimethyl-3-octenedinitrile, and approximately 1 weight percent of the combination of 2,6-dimethyl-4-methyleneheptanedinitrile and 2,4,6-trimethyl-3-heptenedinitrile. For convenience, this mixture will hereinafter be referred to as diadduct. The catalytic hydrogenation of diadduct results in the formation of a mixture of saturated amines which is composed primarily of 5-methylnonanediamine.

In each of the runs described in the examples below, a 0.5-inch (12.7 mm) diameter by 20-inch (508 mm) length continuous reactor fitted with a steam heating system and a temperature recorder and containing about 20 g of the supported catalyst was used. The reactor was flushed with nitrogen, flushed with hydrogen at a rate of 1 liter/minute, and heated to 100° C. A mixture containing diadduct, 2-methyl-2-propanol, and ammonia in a weight ratio of 1/8/1 was fed to the reactor at a liquid hourly space velocity of about 6. Reactor conditions during the hydrogenation runs were 1000 psig (6.9 MPa) pressure, 100° C. and 1 liter/minute hydrogen flow.

Samples were collected from the reactor effluent after 4 hours of run time and after 19 hours of run time and were analyzed for reaction product composition by vapor phase chromatography after removal of the 2-methyl-2-propanol and ammonia under reduced pressure.

The catalysts used in Examples I through III were prepared by impregnating the support with rhodium chloride or rhodium nitrate from an aqueous solution after allowing the support to stand in contact with the aqueous solution overnight and drying the impregnated support at 120° C. under 5 to 10 mm Hg vacuum for 5 hours (run 4), 6 hours (run 3) or overnight (about 15 hours—runs 1, 2, 5, 6, 7, 8 and 9). The impregnated, dried support was then reduced in the presence of hydrogen at 400° C. for 3 hours. The catalysts used in Examples IV through VI were prepared by several procedures described in the examples. The amounts of metal in the catalysts in the examples are expressed as weight percent metal based on the weight of the support. All mesh sizes are U.S. Standard Sieve Series, ASTM Specification E-11-61.

The surface area measurements in the examples were made by the BET method using nitrogen adsorption. The pore volumes were determined by water adsorption using the Innes method. An Aminco 5-7125B Porosimeter was used with mercury to determine the pore size distribution and the average pore size was calculated from the distribution.

EXAMPLE I

Two control runs were carried out in which the diadduct was hydrogenated in the presence of 0.5 weight percent rhodium on alumina ($Rh/Al_2O_3$) catalysts. The alumina support in run 1, a $\gamma$-alumina in the form of $\frac{1}{8}$-inch pellets, was a commercial support from Harshaw Chemical Company. Run 2 used a T-1370 8 to 20 mesh granular $\gamma$-alumina support from United Catalyst & Chemicals Company. The results of the runs are summarized in Table I.

| Run | Rh Catalyst Support | Saturated Diamine in Product, wt. %[a] | |
|---|---|---|---|
| 1 | $\gamma$-alumina pellets | 53[b] | 38[c] |
| 2 | $\gamma$-alumina granules | 78[b] | 21[c] |

[a]Weight percent saturated diamines in reaction product mixture after removal of 2-methyl-2-propanol and ammonia.
[b]Run time of 4 hours.
[c]Run time of 19 hours.

The results shown in Table I show that under the described reaction conditions the $Rh/Al_2O_3$ catalysts produced the desired saturated diamine product, but after 19 hours of run time the amounts of product were low. The catalysts were examined after 19 hours and were found to be physically deteriorating.

EXAMPLE II

A series of control runs were carried out in which the hydrogenation of diadduct was attempted in the presence of catalysts containing 0.5 weight percent rhodium on silica supports outside the scope of the present invention. The results of these runs are presented in Table II.

TABLE II

| Run | Support | Surface Area, $m^2/g$ | Pore Vol., mL/g | Ave. Pore Size, A | Saturated Diamine in Product, wt. %[a] | |
|---|---|---|---|---|---|---|
| 3 | Davison G407[b] | 740 | 0.43 | 22 | (f)(h) | (g)(i) |
| 4 | Davison G41[b] | 740 | 0.41 | 22 | 46 | 31 |
| 5 | Houdry HSC534[c] | 200 | 1.0 | 200 | (f) | (f) |
| 6 | Ketjen PA16065[d] | 88 | 0.58 | 264 | 14 | (f) |
| 7 | PPG PP-2[e] | 40 | 0.3 | 900 | 13 | (f) |
| 8 | PPG PP-1[e] | 250 | 0.28 | 125 | (f) | (f) |

[a]See footnote a of Table I.
[b]8 to 20 mesh granules.
[c]7 to 14 mesh granules.
[d]1/16-inch extrudate.
[e]3 mm diameter spheres.
[f]Very little saturated diamine present.
[g]Not determined.
[h]Amounts in this column were determined after 4 hours run time.
[i]Amounts in this column were determined after 19 hours run time.

The results tabulated in Table II show that rhodium on several different silica supports is ineffective for the hydrogenation of diadduct under the conditions used in these runs. Each of the supports has one or more of the characteristics of surface area, pore volume or average pore size outside the ranges defining the present invention.

EXAMPLE III

Run 9 was carried out according to the invention process for the hydrogenation of diadduct with a catalyst containing 0.5 weight percent rhodium on Davison G59 silica. The G59 support was an 8 to 20 mesh granular silica support with a surface area of 340 m²/g, a pore volume of 1.15 mL/g and a pore size of 135 Å.

After 4 hours of run time, the product contained 97 weight percent of saturated diamines and after 19 hours of run time the product contained 95 weight percent saturated diamines. The catalyst showed no signs of disintegration or collapse at the conclusion of the run. A comparison of these results with the result of the runs reported in Examples I and II using various alumina and silica supports clearly demonstrates the improvements in catalyst physical stability and in catalyst activity with the supported rhodium catalyst of the invention.

EXAMPLE IV

A series of hydrogenation runs was carried out to demonstrate the importance of the catalyst preparation procedure on the hydrogenation of diadduct over a catalyst containing 0.5 weight percent rhodium on a Davison G59 silica support. In each run the G59 silica support was impregnated with rhodium chloride from an aqueous solution by evaporating the water with a rotary evaporator after soaking the support in the aqueous solution overnight. In run 10, the impregnated support was not treated further before reduction. In run 11, the impregnated support was dried at 350° C. for three hours in a flowing $N_2$ atmosphere before reduction. In run 12, the impregnated support was dried at 100° C. for 4 hours under a 2 mm Hg vacuum. All three catalysts were then reduced in the presence of hydrogen at 400° C. for 3 hours. The results of these runs are shown in Table III.

TABLE III

| Run | Catalyst Prep[a] | Saturated Diamine in Product, wt. %[b] | |
|---|---|---|---|
| 10 | No additional treatment | 84[c] | 59[d] |
| 11 | $N_2$ stream, 350° C., 3 hrs. | 88 | 45 |
| 12 | 2 mm Hg, 100° C., 4 hrs. | 95 | 87 |

[a]The support was impregnated with $RhCl_3$ before the indicated treatment, after which the impregnated support was reduced with hydrogen.
[b]See footnote a in Table I.
[c]Amounts in this column were determined after 4 hours run time.
[d]Amounts in this column were determined after 19 hours run time.

The results of runs 10, 11 and 12 demonstrate the effect of the catalyst preparation procedure on the activity of the resulting catalyst. The preparation in run 12 included vacuum treatment before reduction and resulted in a substantial increase in the amount of saturated diamine in the hydrogenation product as compared with runs 10 and 11. The catalysts in runs 10, 11 and 12 showed no signs of collapse at the conclusion of the runs. The invention catalyst of run 12 showed a relatively slow decline in catalyst activity during the course of the testing period.

EXAMPLE V

Two control runs were carried out in which diadduct was hydrogenated over 0.5 weight percent rhodium on alumina catalysts which had been prepared by procedures similar to two of the procedures described in Example IV. These runs show the effects of varying the preparation procedures for rhodium catalysts on a support other than the support of the invention catalyst. In both runs a United Catalyst & Chemicals Company T-1370 8 to 20 mesh granular γ-alumina support was impregnated with rhodium chloride from an aqueous solution by soaking the support in the aqueous solution for about 4 hours. In run 13, the impregnated support was not treated further until the reduction. In run 14, the impregnated support was dried at 125° C. and 5 to 10 mm Hg vacuum overnight (about 15 hours). Both impregnated supports were reduced in the presence of hydrogen at 400° C. for 3 hours. The results of these runs are shown in Table IV.

TABLE IV

| Run | Catalyst Prep[a] | Saturated Diamine in Product, wt. %[b] | |
|---|---|---|---|
| 13 | No additional treatment | 66[c] | 16[d] |
| 14 | 2 mm Hg, 100° C., 4 hrs. | 53[c] | 39[d] |

[a]See footnote a of Table III.
[b]See footnote a of Table I.
[c]Run time 4 hours.
[d]Run time 19 hours.

The results tabulated in Table IV show that for a $Rh/Al_2O_3$ catalyst, a preparation procedure involving vacuum treatment (run 14) resulted in a decrease in the desired product after 4 hours and an increase in the product after 19 hours compared with the results of a run using a catalyst prepared without a vacuum step (run 13). In addition, the catalyst of run 14 showed signas of collapse at the conclusion of the run. Runs in Example IV demonstrated the substantial improvement in product formation at both sampling periods and good physical stability of a rhodium/G59 silica catalyst, particularly when prepared using a vacuum treatment.

EXAMPLE VI

Several additional control runs were carried out in which the diadduct was hydrogenated over a ruthenium catalyst on either a Davison G59 8 to 20 mesh silica support or a United Catalyst & Chemicals Company T-1370 8 to 20 mesh γ-alumina support. The catalysts contained 0.5 weight percent ruthenium and were prepared by various procedures to demonstrate that ruthenium catalysts on a G59 silica support are less sensitive to the preparation procedure than the rhodium/G59 catalyst described in Example IV and that, unlike the rhodium/G59 catalyst, a ruthenium catalyst on an alumina support is adversely affected by vacuum treatment. In all runs the support was impregnated with ruthenium chloride from an aqueous solution after soaking the support in the aqueous solution overnight. In runs 15 and 18, the impregnated support was not treated further before reduction. In runs 16, 17 and 19, the impregnated supports were dried at 100° C. and 2 mm Hg vacuum for 4 hours before reduction. All of the impregnated supports were then reduced in the presence of hydrogen at 400° C. for 3 hours. The results of the hydrogenation runs with these catalysts are shown in Table V. Runs 16 and 17 are duplicate runs and are included to show reproducibility of the hydrogenation runs.

TABLE V

| Run | Catalyst | Catalyst Prep[a] | Saturated Diamine in Product, wt. %[b] | |
|---|---|---|---|---|
| 15 | Ru/G59 | No additional treatment | 78[c] | 36[d] |
| 16 | Ru/G59 | 2 mm Hg, 100° C., 4 hrs. | 80 | 58 |
| 17 | Ru/G59 | 2 mm Hg, 100° C., 4 hrs. | 79 | 59 |
| 18 | $Ru/Al_2O_3$ | No additional treatment | 85 | 62 |
| 19 | $Ru/Al_2O_3$ | 2 mm Hg, 100° C., 4 hrs. | 75 | 50 |

[a]See footnote a of Table III.
[b]See footnote a of Table I.
[c]Run time of 4 hours.
[d]Run time of 19 hours.

The results of runs 15, 16 and 17 show that a ruthenium on silica catalyst is less sensitive to catalyst preparation procedure than the invention rhodium on G59 silica catalyst as shown in runs 10, 11 and 12 of Example IV. Runs 16 and 17 used catalysts prepared using vacuum treatment and were approximately equal in activity after 4 hours and were superior after 19 hours of run time than the run 15 catalyst, which was not subjected to vacuum treatment.

Runs 18 and 19 show that a ruthenium/Al$_2$O$_3$ catalyst preparation involving vacuum treatment resulted in less activity than a ruthenium/Al$_2$O$_3$ catalyst prepared without vacuum treatment.

That which is claimed is:

1. A process for preparing a hydrogenation catalyst comprising the steps of contacting a silica support having a surface area of at least about 275 m$^2$/g, a pore volume of from about 1.0 to about 1.5 mL/g and an average pore size of from about 100 to about 175 Å with a liquid solution of a substance selected from rhodium and reducible compounds of rhodium so as to incorporate within the hydrogenation catalyst from about 0.05 to about 30 weight percent of rhodium;

drying the thus-contacted silica support under a vacuum of from about 10$^{-4}$ to about 20 mm Hg at a temperature of about 20° to about 250° C. for a time of about 15 minutes to about 30 hours; and contacting the thus-dried silica support with a reducing agent under reducing conditions to produce a rhodium-containing hydrogenation catalyst.

2. The process of claim 1 in which the vacuum treatment is carried out at from about 10$^{-2}$ to 20 mm Hg, a temperature from about 40° to about 200° C. and a time of from about 1 hour to about 24 hours.

3. The process of claim 1 in which the reducible compounds of rhodium are selected from the group consisting of rhodium oxides, halides, nitrates, oxalates, acetates, carbamates, propionates, tartrates, hydroxides and mixtures of these.

4. The process of claim 1 in which the reducible compounds of rhodium are selected from rhodium chloride and rhodium nitrate.

5. The process of claim 1 in which the reducing agent is selected from the group consisting of hydrogen, hydrazine and sodium borohydride.

6. The process of claim 1 in which the reduction step is carried out during the hydrogenation of the at least one unsaturated dinitrile and the reducing agent is hydrogen.

7. The hydrogenation catalyst prepared by the method of claim 1, 2, 3, or 5.

8. The process of claim 1 in which the silica support is contacted prior to vacuum treatment with a material consisting essentially of a liquid solution of a substance selected from rhodium and reducible compounds of rhodium.

9. The process of claim 1 in which the silica support is contacted with a material consisting essentially of a liquid solution of rhodium chloride or rhodium nitrate.

* * * * *